United States Patent [19]
Efthymiou

[11] 3,950,227
[45] Apr. 13, 1976

[54] BATCH METHOD OF ESTABLISHING AND MAINTAINING A CONTROLLED AEROBIC ENVIRONMENT FOR A MICROBIAL CULTURE

[75] Inventor: Constantine Efthymiou, Kew Gardens, N.Y.

[73] Assignee: St. John's University, New York, N.Y.

[22] Filed: Dec. 12, 1973

[21] Appl. No.: 424,083

Related U.S. Application Data

[62] Division of Ser. No. 99,952, Dec. 21, 1970, Pat. No. 3,793,154.

[52] U.S. Cl............................ 195/109; 195/103.5 R
[51] Int. Cl.² ............................................ C12B 1/14
[58] Field of Search...... 195/109, 142, 143, 103.5 R

[56] References Cited
UNITED STATES PATENTS

| | | | |
|---|---|---|---|
| 3,010,881 | 11/1961 | Markhof | 195/109 |
| 3,407,120 | 10/1968 | Weiss et al. | 195/142 |
| 3,609,327 | 9/1952 | Kolachov et al. | 195/142 |
| 3,645,846 | 2/1972 | Imada et al. | 195/109 |
| 3,647,632 | 3/1972 | Johnson et al. | 195/142 |

*Primary Examiner*—Alvin E. Tanenholtz
*Attorney, Agent, or Firm*—Kenyon & Kenyon

[57] ABSTRACT

A flask for establishing and maintaining environmental control for microbial cultures. The flask has a body resembling an erlenmeyer flask, and a screw capped large opening in the top thereof. The flask also has three sidearm tubes extending through its walls, one for outlet of gas from the flask, and another, extending into the flask to a point near its bottom, which functions as a gas input conduit. A third sidearm tube is provided for inoculation of the flask and sampling of its contents. Each sidearm is provided with a septum-type plug and a perforated screw cap to hold the plug in sealing position. The plugs and caps permit aseptic injection and withdrawal of gas or liquid to and from the flask by means of hypodermic needles inserted through the caps and plugs without disturbing the atmospheric conditions established within the flask. Methods for use of the apparatus for establishing and maintaining aerobic and anaerobic environmental systems are also disclosed.

1 Claim, 5 Drawing Figures

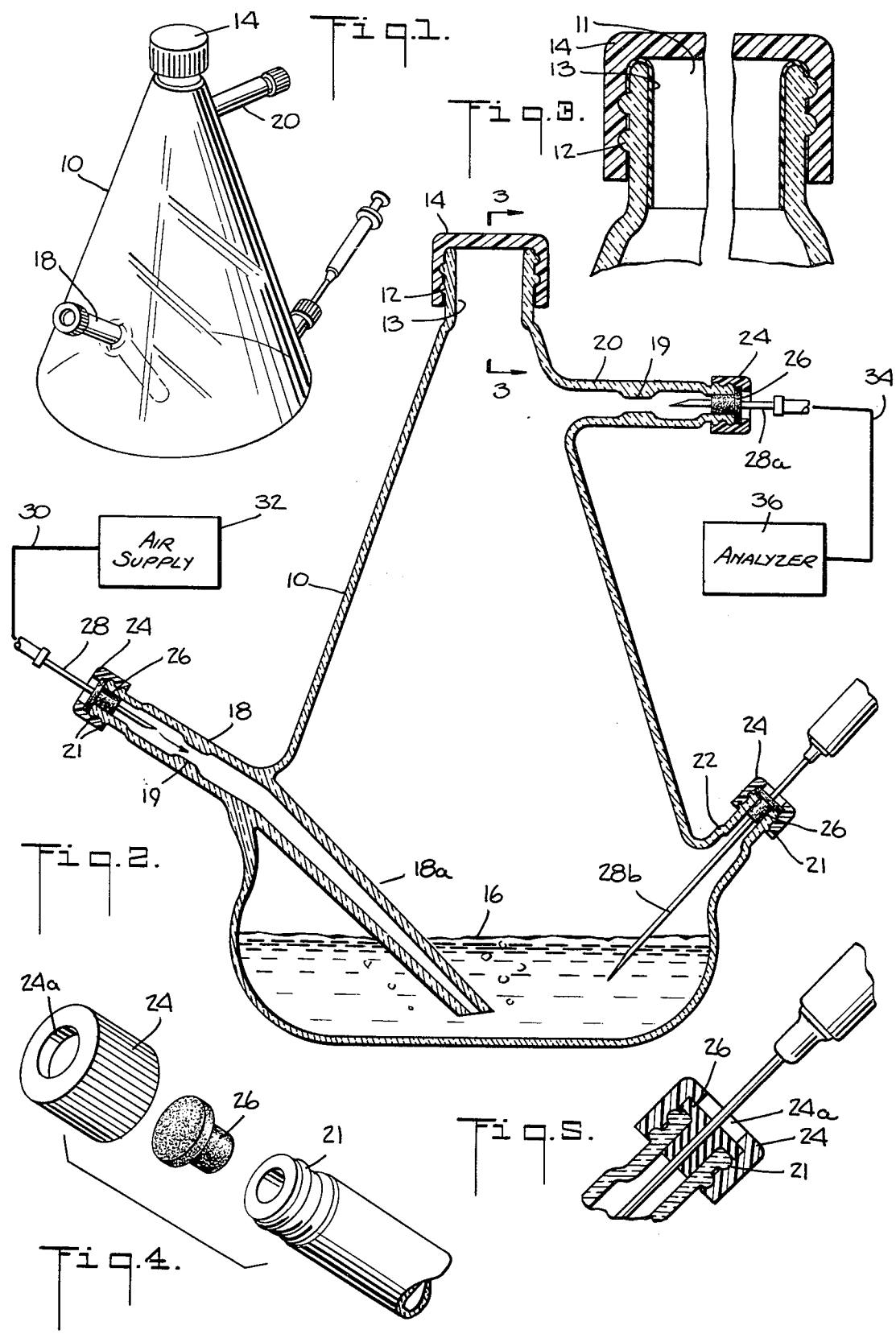

BATCH METHOD OF ESTABLISHING AND MAINTAINING A CONTROLLED AEROBIC ENVIRONMENT FOR A MICROBIAL CULTURE

This is a division of application Ser. No. 99,952, filed Dec. 21, 1970, now U.S. Pat. No. 3,793,154.

BACKGROUND OF THE INVENTION

1. Field of the Invention

This invention is directed to the field of laboratory apparatus and methods and particularly to laboratory vessels and methods for enabling economical establishment and maintenance of optimum environmental conditions for growing microbial cultures in either aerobic or anaerobic systems.

2. Prior Art

One of the most useful laboratory procedures in biological research is the growing of sample cultures of microbes in small vessels. It has long been common to grow such cultures in conventional erlenmeyer flasks, the cultures being placed, or inoculated, into a liquid medium hospitable to their growth, the flasks being plugged with some sort of porous material such as cotton, gauze, or foam.

Microbial cultures, depending on their type, may require aerobic or anaerobic environments.

It is critical to microbial cultures requiring aerobic environments that they receive sufficient oxygen. A paucity of oxygen is detrimental to optimum growth of the cultures, due to the resultant inhibition of the metabolic activity directly related to the oxidative process of the microbes. Research further indicates that lack of oxygen is also detrimental to the integrity and longevity of cells comprising the culture.

Microbial cultures derive their oxygen from that supply of oxygen which is dissolved in the liquid medium in which they are located. The conventional erlenmeyer flask is incapable of allowing sufficient oxygen transfer into the medium to satisfy the requirements of many types of microbes.

A liquid medium in a conventional erlenmeyer flask receives oxygen by means of transfer of oxygen into the medium from above the surface of the medium in the flask. The rate of transfer is directly related to the surface area of the air-medium interface. Since the surface area of the medium in a flask does not increase with increasing volume of medium, (indeed, it decreases in the case of flasks which narrow toward their tops) it becomes more difficult to maintain a sufficiently high oxygen level in a medium as its volume rises. Therefore, in the conventional flask, the amount of medium which can be used, and consequently the size of the culture that can be grown, are limited because the supply of oxygen that can reach the growing cells becomes more limited as the liquid volume within the flask is increased.

It is one object of this invention to provide for growth of microbial cultures in which ample oxygen can be transferred to the medium regardless of the surface-to-volume ratio of the medium.

Another limitation in the conventional methods of growing cultures is that the plugs used in the flasks, although permeable to the air, do limit the entry of air to the flask. It is a purpose of this invention to provide a method in which the entry of oxygen into a flask is not dependent upon its passage through conventional porous plugs.

It has been found that, in connection with the use of erlenmeyer flasks, greater oxygen transfer can be obtained by shaking the flasks by means of mechanical shaking machines. These shaking machines are frequently run, in practice, at standard speeds, and often such speeds are not appropriate to provide optimum oxygen transfer. Even where the machine is capable of very rapid shaking (which, on first examination, should yield high oxygen transfer) the efficiency of oxygen transfer is adversely affected by strong vortexing of the liquid medium which takes place in the vessels.

To correct this problem, and to further enhance oxygen transfer in shaken vessels, it is known to add baffles to the interior of the flasks to increase agitation of the liquid medium during shaking, and to reduce vortexing. Difficulties arise with theis technique, however, in the case of culturing of microbes which tend to form filamentous chains. This type of organism, when agitated in a flask having baffles, will tend to grow on the baffles themselves, or on the walls of the flasks, rather than in the medium itself, where optimum growth is obtainable.

A further purpose of this invention is to enable the introduction of abundant oxygen into the growth medium without the use of baffles. Additionally, it is a purpose to enable the introduction of abundant oxygen while lessening and sometimes eliminating the need for shaking of the flask.

Another problem with the conventional cotton, gauze, or foam plugs often used in the tops of erlenmeyer flasks is that these closures, by virtue of their ability to allow air to enter, and, especially at high temperature incubations, will also allow extensive evaporation of the medium and undesirable change in the volume thereof, upsetting the uniformity of the environment, and the quantitation of the contents of the flask.

Microbial cultures growing in a medium emit metabolic products some of which are gaseous or volatile. It is often desirable to analyze quantitatively these products of metabolism. Obviously, the porous plugs commonly used allow these products of metabolism to escape, making their measurement and analysis impossible. Another disadvantage of the use of porous plugs is that it is impossible, without the use of extremely elaborate and expensive laboratory apparatus, to determine with any degree of accuracy the amount of oxygen transferred to the medium and to the microbial culture.

It is a further purpose of this invention to obtain accurate estimation of oxygen absorbed by the microbial culture and quantitative determination of all metabolic products of the culture.

It is another object of this invention to provide an adaptable and relatively inexpensive method to permit variable control of aeration conditions so as to make such conditions optimal for the desired growth, metabolic activity, or viability of a given microorganism.

In prior art flasks, due to their incapability of air-tight sealing, the mechanical pressure of the gaseous phase of the microbial system cannot be regulated. Consequently, such flasks are of little or no utility in aerobic experiments in which oxygen tension is expected to function as a growth limiting factor.

Because of their "loose" closures, sterility in the prior art flasks can be maintained only fortuitously. The flask of this invention offers easy maintenance of internal sterility.

It is another object of this invention to provide an efficient and economical method to permit precise control over environmental conditions of a microbial culture for relatively long periods of time. To this end, this invention provides a laboratory flask with respect to which gaseous or liquid substances can be inserted and removed without substantially disturbing the environmental conditions therein, thus maintaining the stability and balance of the system, while still allowing for controlled changes of variables of the environment and sampling of substances within the flask.

It is still a further purpose of this invention to provide a laboratory method for the efficient and economical maintenance of precisely controlled environmental conditions for growth of microbial systems, said method adaptable to provide both aerobic and anaerobic environments.

The defects of the erlenmeyer flasks referred to above have been recognized by those skilled in the art for some time. Consequently, numerous modifications of the erlenmeyer flask and, indeed, other types of flasks, have been proposed in attempts to overcome these defects. However, all the prior art flasks known to applicant have one or more of the defects referred to above and only the flask and method of this invention successfully attains all of the desired advantages discussed above.

SUMMARY OF THE INVENTION

The environmental control flask has a body of the same general shape as that of the common erlenmeyer flask, tapering toward its top. At the top is a relatively large opening which is provided with a cap which is adapted to seal the opening tightly.

The flask has three sidearm tubes extending through its wall. One of these is a gas outlet tube and is positioned relatively high on the side of the flask. Another is an input tube. This input sidearm extends from outside the flask into the interior downward to a point near the bottom where its diameter is the smallest. The input sidearm tube tapers downward, having its smallest diameter at its end. The smallness of the interior orifice of the input sidearm causes the kinetic energy of gas introduced through the sidearm to increase at the point at which it enters the liquid medium, facilitating its diffusion and transfer into the medium. Each of these two sidearm tubes has an internal constriction intermediate along its length. The purpose of these constrictions will be discussed below.

A third sidearm tube, near the bottom of the flask, provides access to the interior thereof for inoculation of the flask, or for sampling its contents. This latter sidearm has no internal constriction.

Each of the sidearm tubes is provided with a septum-type plug, made of silicone rubber, each plug adapted to seal the end of its respective sidearm tube. These plugs are susceptible to penetration by a hypodermic needle and are capable of resealing on withdrawal of the needle.

Each tube is also provided with a phenolic, perforated cap adaptable to firmly cover the end of the tube to hold the associated plug in place, while still allowing penetration of the plug by the hypodermic needle.

This invention also involves methods of using the apparatus to provide efficient and economical maintenance of aerobic and anaerobic environments for microbial cultures.

With respect to aerobic systems, a needle, connected to a supply of purified air or oxygen, is inserted through the plug in the input sidearm, and a measured quantity of air or oxygen is carried directly into the medium in the flask. If exhaust of metabolic products is desired, it can be provided via a second needle inserted through the plug in the outlet sidearm. Sampling or inoculation can be accomplished by a needle passing through the plug in the third, or inoculum, sidearm.

A anaerobic system can be established by flushing the flask, through a needle in the input sidearm, with purified nitrogen, or a suitable mixture of carbon dioxide and nitrogen, and by then inoculating the medium and removing the needle. Alternately, gaseous metabolic products can be removed simultaneously by inserting nitrogen and withdrawing the gas from above the medium via the output sidearm.

BRIEF DESCRIPTION OF THE DRAWINGS

FIG. 1 is a perspective view of the environmental control flask of this invention, showing employment of a hypodermic needle to provide access to its interior.

FIG. 2 is a side view of the flask showing the various caps and plugs associated therewith, and support facilities used to establish optimum environment for a microbial culture.

FIG. 3 is a side section view of the closure for the top of the flask.

FIG. 4. is an exploded view of the closure apparatus for the sidearm tubes.

FIG. 5 is a side section view of the closure apparatus for the sidearm tubes.

DESCRIPTION OF THE PREFERRED EMBODIMENT

The flask of this invention includes a body 10 having a general shape resembling that of the common erlenmeyer flask, traditionally used in laboratories. Body 10 is most suitably made of an inert transparent material, glass being the traditional material for most laboratory vessels.

At the top of body 10 is a large opening 11 designed to accommodate bulk filling and cleaning of body 10. The interior of body 10 adjacent opening 11 is lined with a teflon coating, to reduce tendency of particulate matter to cling to the inside thereof, and to provide a tight fit for screw cap 14 which is adapted to close opening 11, by means of engagement with threads 12 around the outside of the top of body 10. The coating is designated 13.

Body 10 is provided with three sidearm tubes. Gas input sidearm 18 is located about 6 centimeters from the bottom of body 10 and extends outwardly therefrom at approximately a 30° angle to the horizontal. Extension 18a of input sidearm 18 also extends into the interior of body 10 downwardly at an angle of approximately 45°, to a point about 5 millimeters from the bottom of body 10. Extension 18a tapers downwardly, having its smallest diameter at its tip. Input sidearm 18 has an overall diameter of approximately 10 millimeters, and is provided with internal constrictions 19 at a point intermediate along its length.

It is contemplated that the flask of this invention be adaptable for use with conventional cotton stoppers, as well as with the sealing plugs and caps as disclosed herein. The internal constrictions 19 aid in accomplishing this purpose by providing means to prevent such cotton stoppers from falling into the flask, and from being sucked into the flask as a result of gas currents established through the tubes during utilization of the flask.

Located closer to the top of body 10 is gas outlet sidearm 20, extending outwardly from body 10 in roughly horizontal direction. The overall diameter of sidearm 20 is approximately the same as that of sidearm 18, and sidearm 20 is provided with internal constriction 19, similar to those of sidearm 18.

The third sidearm is incoulum sidearm 22 extending outwardly and upwardly at approximately a 30° angle from a point on body 10 approximately 5 centimeters from its bottom. Inoculum sidearm 22 has no internal constriction.

Each sidearm tube is provided with a rubber silicone septum-type stopper, each stopper being insertable into the end of its associated sidearm for the purpose of sealing it tightly.

Each sidearm tube is also provided with a phenolic screw cap 24, having perforation 24a in its end surface, and which is adapted by engagement with threads 21 on the end of each associated sidearm tube to firmly hold its associated plug 26 in sealing position in the mouth of its sidearm.

Plugs 26, being made of silicone rubber, provide an air-tight seal when positioned in the ends of the sidearms. Nonetheless, plugs 26 are susceptible of penetration by hypodermic needles 28, so that gas or liquid substances can thereby be introduced into or withdrawn from the interior of the flask. Perforations 24a enable needles 28 to be inserted through plugs 26 while caps 24 maintain each of plugs 26 firmly in the ends of the sidearms. When needle 28 is withdrawn from plugs 26 and through cap 24, the silicone rubber comprising plug 26 immediately reseals tightly to prevent any more liquid or gas from passing through the associated sidearm. In this way, gas or liquid substances can be inserted into or withdrawn from any of the sidearms without removal of the plugs, and the plugs immediately reseal on withdrawal of the needle.

OPERATION

This invention can be used for the establishment and maintenance of optimum environmental conditions for microbial cultures on a "batch" basis. It is adaptable for the establishment of either aerobic or anaerobic environments.

For the establishment of precisely known aerobic conditions, the flask is cleaned and the liquid medium in which the culture is to grow is placed therein. The level 16 of the surface of the liquid medium is made high enough so that the tip of sidearm extension 18a is submerged in the medium. Screw cap 14 is closed upon opening 11 and all of the plugs 26 and screw caps 24 are positioned to seal all the sidearms. After heat sterilization of the medium, a microbial culture is then introduced into the medium through inoculum sidearm 22, by means of needle 28b. Heat labile components of the medium are introduced into it in the same way prior to inoculation.

Hypodermic needle 28, connected to rubber tubing 30, which is in turn connected to a supply 32 of purified and filtered air, is inserted into sidearm 18 through perforation 24a so that it extends through plug 26. A second hypodermic needle 28a is inserted through the screw cap 24 and plug 26 located in the end of outlet sidearm 20. Needle 28a is connected to output analysis apparatus 36.

Purified, filtered and precisely metered air is thus introduced into sidearm 18 through needle 28, and is allowed to bubble up through medium 16, in order that the oxygen in the air may dissolve into the medium, and subsequently be available to the culture. Agitation of the flask on a mechanical shaker, operated during incubation, will further enhance the rate and uniformity of oxygen diffusion throughout the medium. Excess air entering the flask, and gaseous products of metabolism of the microbial culture, exit by way of output sidearm 20 and needle 28a. Such effluent gas may then be conducted to analysis apparatus 36, which can be adapted to perform any desired analysis.

It is seen that in the use of this apparatus, the amount of oxygen supplied to the medium and available to the culture is not dependent on seepage into body 10 through a porous plug, as is the case in the conventional-stoppered erlenmeyer flask. Abundant oxygen can be supplied, and the precise amount entering can be metered and governed. Moreover, the bubbling of the air through the medium enables the medium to absorb much more oxygen than can be absorbed by simple surface transfer, as in the prior art. It is further clear that the effluent gases, instead of haphazardly escaping through a porous plug, can be withdrawn in precise volumes or allowed to escape through a conduit which can accumulate such gas for storage or direct it to analysis apparatus for further study. Also, the method of introducing oxygen which is made possible by this apparatus renders the oxygen transfer into the medium independent of the ratio between surface area of the medium and the volume thereof. The transfer rate can be changed by merely altering the volume of air introduced under pressure through sidearm tube 18. Sterility of the interior of the flask can easily be maintained, and, due to the sealing properties of the plugs, internal pressure of the flask can vary from the atmospheric level.

Access to the medium itself for the purpose of inoculation or of sampling the culture is made available by inoculum sidearm 22. Entry through the sidearm can be made by use of a hypodermic needle. Measurement of growth of the culture can be made by aseptically withdrawing culture samples at fixed intervals of time. Turbidimetric, total count, and dry weight measurements can be obtained in this way. Also, chemical analysis can be made of products in the solution, along with enzyme assays.

Analysis of the gaseous products of metabolism can be made by carrying the effluent gas extracted from sidearm 20 through a conventional fermentation train. Profiles of the components of the effluent gas can be determined by conventional gas liquid chromotography done on small samples.

This flask is also adaptable for the establishment of anaerobic conditions. To accomplish this, a flask is autoclaved, after the addition of the medium. The flask is then flushed for about thirty-five minutes with a constant stream of pre-purified nitrogen injected by a needle through gas input sidearm 18, and which is removed by a needle from gas outlet sidearm 20. The nitrogen can be purified by passing through acid dichromate and sterile cotton.

The flask is then inoculated through the inoculum tube 22 and is incubated as a stationary culture in an atmosphere of nitrogen, the flask being sealed by withdrawal of the needles from the sidearms, and sealing all openings.

An alternative method for establishment of anaerobic conditions can be provided where it is desired to carry away the gaseous products of the culture. In this alternative method, the flask is flushed and inoculated in the manner described above. It is then, however, placed on a shaker where it is skaken continuously, and pre-purified nitrogen is continuously pumped into the medium through gas input sidearm 18. This entering nitrogen serves to displace whatever gases are present above the medium out through the gas outlet sidearm 20, provided that needle 28a is inserted through plug 26 to allow the said gases to escape.

It has been shown, by substantial experimentation, that the flask and method of this invention do in fact make possible the establishment and maintenance of microbial growth conditions superior to those obtainable in any prior art known to applicant.

The details of some of this experimentation are set forth in the tables which follow.

Table I is a comparison of growth yields of *Streptococcus faecalis* ATCC 11700 organism grown in the environmental control flask of this invention. The cultures were grown under both aerobic and anaerobic conditions, and in media having glucose concentrations of 2, 4, 6, 8, and 10 micro-moles/ml. In the case of each culture, the dry weight of the cells produced was determined, and the molar growth yield, which is the ratio of dry weight to glucose utilized, was computed, according to the method described by Bauchop, T. and S. R. Elsden, in *The Growth of Microorganisms in Relation to Their Energy Supply*, Journ. Gen. Microbiology 23: 457–469 (1960). The figures are given as follows:

TABLE I

| Incubation Conditions | Glucose Utilized (micromoles/ml) | Dry Weight (micrograms/ml) | Molar Growth Yield |
|---|---|---|---|
| Aerobic — Forced aeration is shaken Environmental Control (EC) Flask (Air Flow: 100 ml/min) | 2 | 280 | 67.0 |
| | 4 | 410 | |
| | 6 | 540 | |
| | 8 | 670 | |
| | 10 | 800 | |
| Anaerobic — Sealed E.C. Flask under nitrogen atmosphere | 2 | 100 | 38.0 |
| | 4 | 180 | |
| | 6 | 260 | |
| | 8 | 340 | |
| | 10 | 420 | |

These yields of *Streptococcus faecalis* are substantially greater than any yields of this organism made possible by any prior art apparatus or methods known to applicant.

The yields of the highest-yielding prior art methods of culturing this organism are set out in the following Table II, citations to the literature describing the prior art methods being set out in footnotes below the table.

TABLE II

| Molar Growth Yield | | Prior Art References |
|---|---|---|
| Aerobic Conditions | Anaerobic Conditions | |
| 43.8 | 27.9 | (1) |
| 58.2 | 21.5 | (2) |
| 46.4 | | (3) |
| 26.8 | 16.0 | (4) |

(1) Deibel, R. H. and M. J. KVETKAS Fumerate Reduction and its Role in Diversion of Glucose Fermentation by Streptococcus Faecalis. Journ. of Bacteriology 88: 858–864 (1964);
(2) Smalley, A. J., P. Jahrling and P. J. Van Demark, Molar Growth Yields as TABLE II-continued

| Molar Growth Yield | | Prior Art References |
|---|---|---|
| Aerobic Conditions | Anaerobic Conditions | |

Evidence for Oxidative Phosphorylation in Streptococcus Faecalis Strain 10C1. Journ. of Bacteriology, 96: 1595–1600 (1968);
(3) Moustafa, H. and E. G. Collins, Molar Growth Yield of Streptococcus Faecalis on Pyruvate, Journ. of Bacteriology, 97: 1496–1497 (1969); and
(4) Bryan-Jones, D. G. and R. Whittenbury, Haematin-Dependant Oxidative Phosphorylation in Streptococcus Faecalis. Journ. of Gen. Microbiology, 58: 247–260 (1969).

It can be seen from Tables I and II that the flask of this invention provides aerobic growth yield which is more than 15% greater than the highest previously reported value, and is much higher than the values for other reported prior art operations which employed various methods lacking in oxygen-supply efficiency.

Furthermore, the anaerobic growth yield obtained by use of this invention exceeds by more than 35% the highest prior art value, and exceeds the other reported values by much more.

It has also been demonstrated that longevity of the cultured organisms is increased by use of the inventive apparatus and method.

*Streptococcus faecalis* cultures were grown for 50 hours by three methods, and turbidity measurements of the cultures were made at intervals over that period, to determine the density of cells in each culture. The results of this work are set out in Table III, for conditions of: forced aeration in the environmental control flask (A); aerobic growth in shaken, cotton-stoppered erlenmeyer flasks, (B); and anaerobic growth in sealed environmental flasks in a nitrogen atmosphere (C).

TABLE III

| Hours after Inoculation | Optical Density at 660 nm (×2) | | |
|---|---|---|---|
| | A | B | C |
| 5 | .394 | .430 | .253 |
| 6 | .494 | .508 | .356 |
| 7 | .581 | .609 | .446 |
| 8 | .704 | .712 | .531 |
| 9 | .800 | .800 | .615 |
| 10 | .800 | .800 | .610 |
| 15 | .758 | .700 | .593 |
| 25 | .800 | .692 | .555 |
| 50 | .761 | .590 | .462 |

This table shows that the culture grown under condition (A) showed remarkable levels of growth which remained almost the same for the duration of the incubation period, in contrast to cultures grown under the common condition (B). Turbidity values under (A) were reduced, at 50 hrs., by only 5% from their peak, while they were reduced more than 25% under (B) and 40% under (C). It is noted that the results of this experiment were corroborated by dry weight and viable count measurements, as well as the optical density (turbidity) measure.

It is evident that this invention provides a small and efficient apparatus in which optimum environmental conditions for a microbial culture can be maintained for a very long time. Furthermore, the closures on the sidearms permit insertion or withdrawal of liquids or gases from the apparatus without breaking its seal and exposing the system to ambient conditions. This feature assists in maintaining the cellular integrity of the culture, and allowing easy analysis of both the growing culture and the products of metabolism of that culture. In the case of aerobic systems, this invention enables the supply of abundant oxygen through the culture without opening the system to the air outside, and losing the balance and uniformity of condition of the environment provided to the culture.

This disclosure is intended to be illustrative only, and it is understood that one skilled in the art could vary the specific embodiments taught herein without departing from the essence of the invention.

What is claimed is:

1. A batch method of establishing and maintaining a controlled aerobic environment for a microbial culture in a liquid medium present within a sealable vessel having an input tube extending from without the vessel to a point within the vessel near the bottom surface thereof, and having further an outlet tube extending through the wall of the vessel at a point above the lowest point of the input tube, said method comprising the steps of introducing the liquid medium into the vessel in a quantity sufficient to establish the level of the medium above the lowest point of the input tube and below the intersection of the outlet tube with the wall of the vessel;

introducing the microbial culture to the liquid medium;

permitting the culture in the medium to incubate while introducing a metered oxygen-containing gas into the vessel through the input tube so that the gas bubbles up through the liquid medium to dissolve the oxygen into the liquid medium while substantially precluding entry to or exit from the vessel of other gases or liquids, except exit of gases via the outlet tube;

shaking the vessel during incubation;

permitting gases above the surface of the liquid medium to exit from the vessel through the outlet tube, while substantially precluding entry to or exit from the vessel of other gases or liquids, except for the entry of the oxygen-containing gas via the input tube; and directing the effluent gas to an analyzer in a precise volume and analyzing the gas for the gaseous products of metabolism.

* * * * *